US00PP20528P3

(12) United States Plant Patent
Malone

(10) Patent No.: US PP20,528 P3
(45) Date of Patent: Dec. 8, 2009

(54) NECTARINE TREE NAMED 'HORTARINE1'

(50) Latin Name: *Prunus persica*
Varietal Denomination: Hortarine1

(75) Inventor: Michael Malone, Havelock North (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/214,353

(22) Filed: Jun. 18, 2008

(65) Prior Publication Data

US 2008/0320620 P1 Dec. 25, 2008

Related U.S. Application Data

(60) Provisional application No. 60/936,286, filed on Jun. 19, 2007.

(51) Int. Cl.
*A01H 5/00* (2006.01)

(52) U.S. Cl. ..... Plt./190

(58) Field of Classification Search ..... Plt./190
See application file for complete search history.

(56) References Cited

U.S. PATENT DOCUMENTS

PP16,585 P2 * 5/2006 Bradford ..... Plt./190

* cited by examiner

*Primary Examiner*—Susan B McCormick Ewoldt
(74) *Attorney, Agent, or Firm*—Greenlee Winner and Sullivan PC

(57) ABSTRACT

A new and distinct variety of nectarine tree (*Prunus persica*) named 'Hortarine1' is described. The variety results from selection among a population of open-pollinated seedlings of the peach variety known as 'Peacharine' (not patented). The fruit of this new variety has an attractive appearance characterized by yellow skin color with dark red blush, yellow flesh with no anthocyanin present, and intense flavor. The new variety appears suitable for the fresh fruit market and has been named 'Hortarine1'.

4 Drawing Sheets

Genus and species of plant claimed: *Prunus persica.*
Variety denomination: Hortarine1.

BACKGROUND TO THE INVENTION

The present new and distinct variety was originated from an open pollinated population of seedlings derived from the peach variety 'Peacharine' (unpatented). Seedlings were grown in a greenhouse in Havelock North, Hawke's Bay, New Zealand. Seedlings on their own roots were transplanted on a research orchard at Lawn Road, Clive, Hawke's Bay, New Zealand in 1998. Seedlings first fruited in the 2001–2002 season. One seedling was selected in February 2002 and was assigned the breeder code, L35/18 and subsequently named 'Hortarine1'.

The present variety was first asexually propagated in March 2002 at Napier, Hawke's Bay, New Zealand, by budding onto 'Golden Queen' (unpatented) peach seedlings. Trees were field planted in winter 2003 on a research orchard at Lawn Road, Olive, Hawke's Bay, New Zealand. The resulting plants have propagated true to type, demonstrating that the characteristics of the new variety are stable and are transmitted without change through succeeding generations.

The present variety is similar to its parent 'Peacharine' (unpatented) by producing fruit that is very firm and of yellow, aromatic flesh but differs from its parent through smaller fruit size and non-pubescent skin (nectarine).

The present variety is most similar to 'Summer Blush' (U.S. Plant Pat. No. 8002) by producing nectarines that are of globose shape, clingstone and yellow fleshed and maturing in the late season (mid February in Hawke's Bay, New Zealand). However, the present variety is distinguished from 'Summer Blush' by producing fruit that have lower percentage overcolour (45% compared to 85%), smaller fruit size (110 g cf. 185 g), a mucro present on the pistil end, and absence of anthocyanin coloration around the stone. In addition, the present variety has a showy flower compared to a non-showy type flower for 'Summer Blush'.

SUMMARY OF THE INVENTION

The new variety was selected from a population of seedlings derived from open-pollination of the peach variety known as 'Peacharine' (not patented). The new variety was selected in February 2002 from among plants located on land at Hawke's Bay, New Zealand, and was assigned the breeder code, L35/18. The new variety has since been named 'Hortarine1'.

The new variety is characterized as follows:

Plant form and vigor: Trees show low-medium vigor with an open and spreading habit; suitable for cultivation as single leader or multi-leader tree Pollination: Self-fertile Fruiting: Fruit commences ripening in mid-February in Hawke's Bay, New Zealand.

Yield: Low-medium yield of 12 tonnes/ha under the prevailing Hawke's Bay conditions.

Fruit characteristics: A small to medium size nectarine; round fruit shape; skin color is yellow with dark red blush overcolor of up to approximately fifty percent of the surface; flesh color is yellow with no anthocyanin present; clingstone.

Flavor and eating quality: The fruit has strong, aromatic flavor similar to the peach variety 'Peacharine' (not patented); non-melting texture.

Geographical adaptation: Observations indicate that the variety is suitable for regions where annual chill accumulation is approximately 800 hours.

BRIEF DESCRIPTION OF THE DRAWINGS

The accompanying photographs show typical specimens of the foliage and the fruit of the new variety as depicted in colors as nearly true as is reasonably possible in a color representation of this type. The photograph in FIG. 1 was taken shortly after harvest when the fruit was at eating maturity.

DETAILED DESCRIPTION OF THE INVENTION

Figure 1:
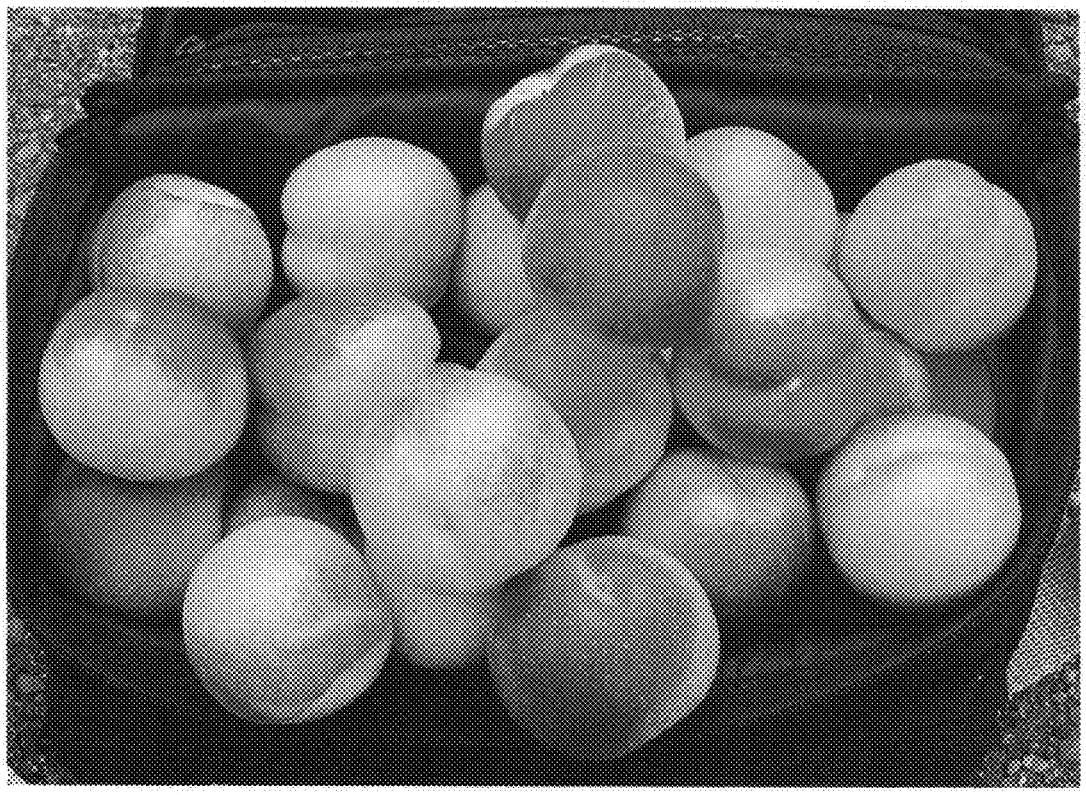
FIG. 1 shows fruit of the present variety.
Figure 2:
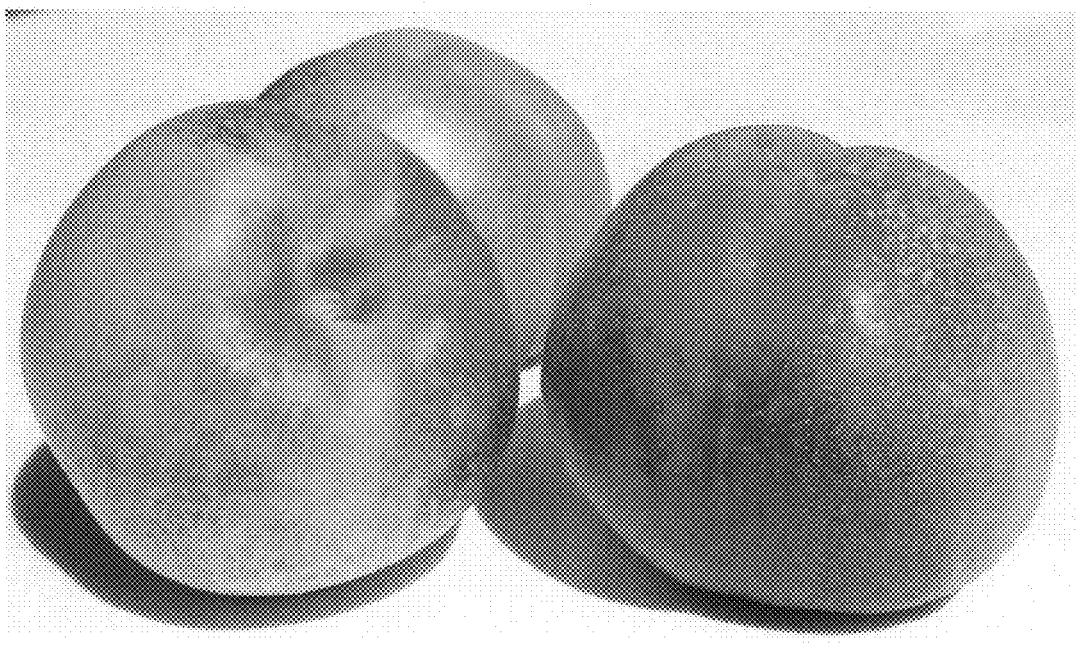
FIG. 2 shows samples of individual fruit of the present variety; view shows blush side, stem end and fruit tip, and fruit suture.
Figure 3:
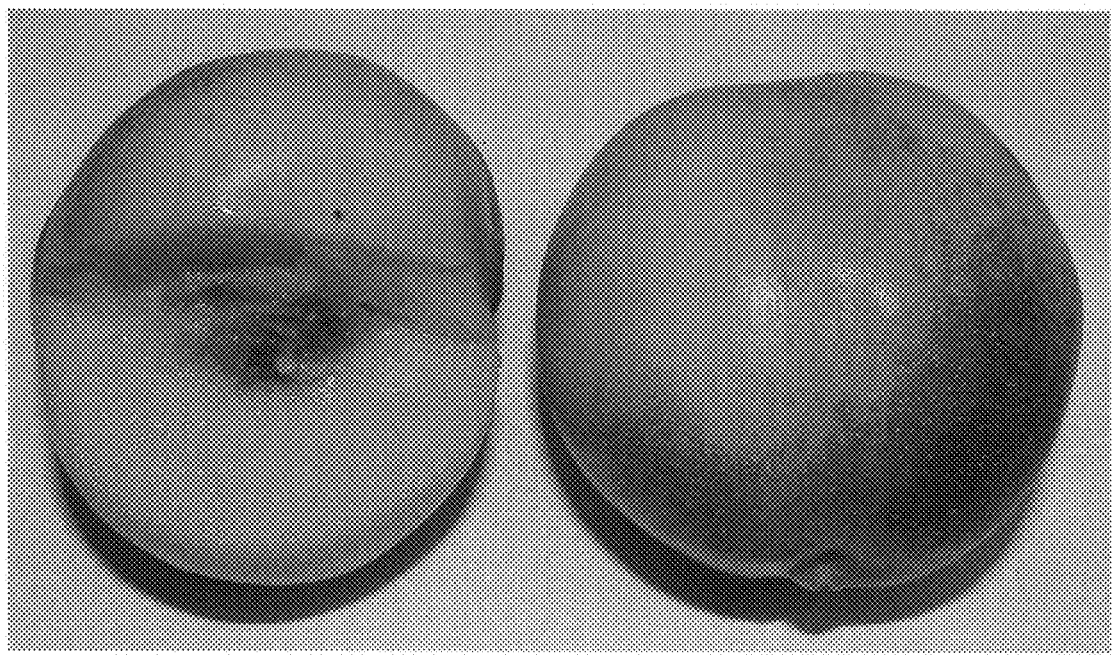
FIG. 3 shows samples of individual fruit of the present variety; view includes cut fruit indicating yellow flesh color with no anthocyanin present.
Figure 4:
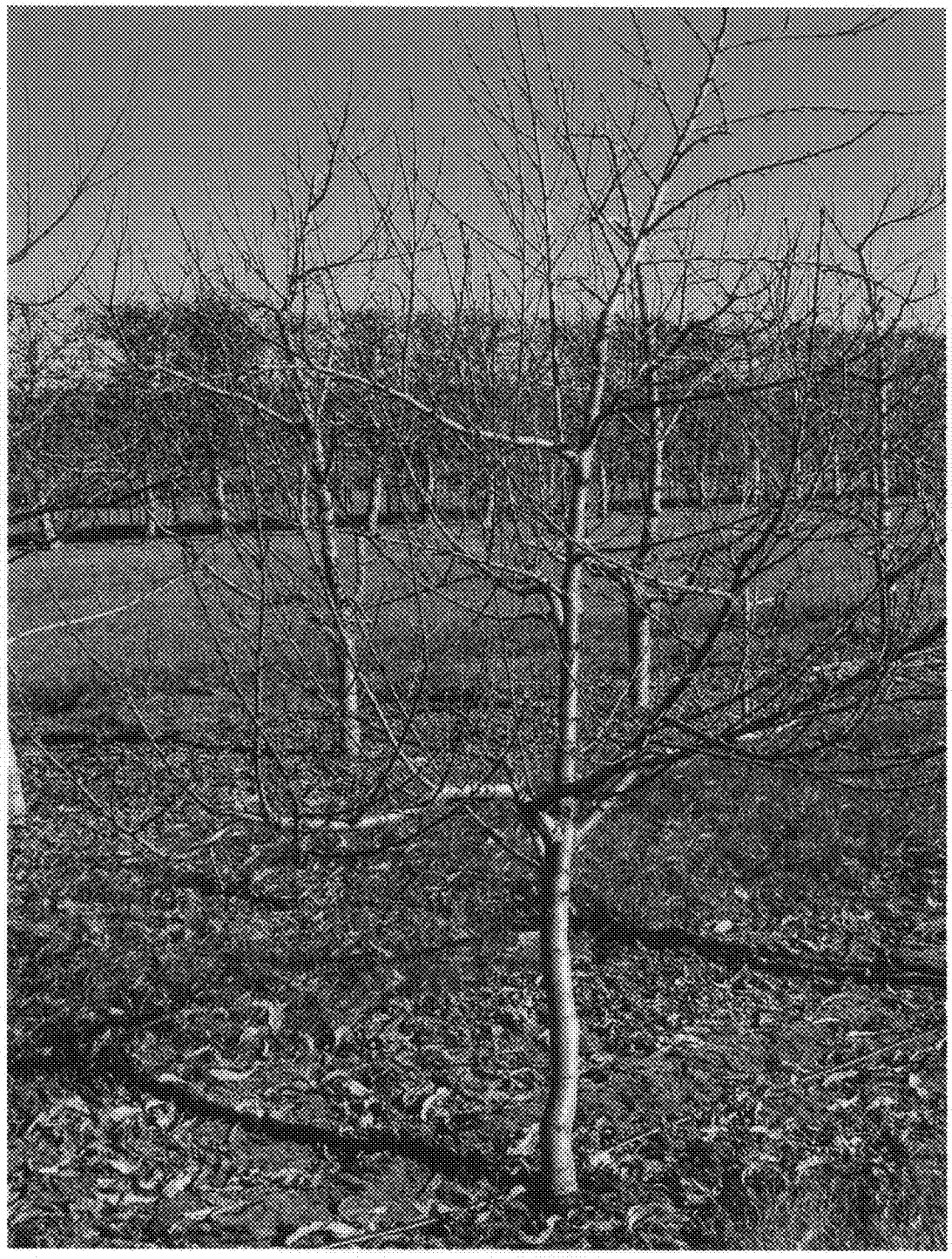
FIG. 4 shows the tree shape and branching development on a 5 year old tree of the present variety budded on 'Golden Queen' seedling rootstock.

The following is a detailed description of the new variety with color terminology in accordance with The Royal Horticultural Society Colour Chart 2001 edition. The specimens described were grown on a research orchard, Lawn Road, Clive, New Zealand. The observations were made in the 2007 season on trees which were four years old at the time, grown on 'Golden Queen' peach rootstock.

Tree:

*Size.*—Small-Medium. Height 2.6 m and 1.7 m diameter under the prevailing cultural practices for central leader trees in Hawkes Bay.

*Form.*—Pruned to central leader, with a spreading growth habit.

*Hardiness.*—Hardy under the prevailing Hawke's Bay conditions.

*Productivity.*—Generally smaller fruit yield because of smaller than average fruit size and sparse flowering under Hawke's Bay conditions; typically about 12 tonnes per hectare.

*Fertility.*—Self-fertile.

*Bearing.*—Regular, alternate bearing not observed.

Trunk:

*Size.*—Small-Medium. 5.6 cm diameter at 20 cm above gound level.

*Texture.*—Smooth.

*Color.*—Grey-brown 199B.

Branches:

*Branch diameter.*—Bottom tier at 53 cm above ground level 10 cm from main trunk typically 3.0 cm diameter. Second tier at 109 cm above ground level 10 cm from main trunk is 2.6 cm diameter.

*Size.*—Typically length of annual growth of one year old shoots ranges from 29.0 cm to 59.0 cm.

*Branch color.*—Grey-brown 199A.

*One year old dormant shoot color.*—Greyed-purple 183B.

*One year old dormant brindille.*—Anthocyanin present — Greyed-purple 183B.

*One year old dormant brindille.*—Anthocyanin absent — Yellow-green 144B.

*Texture.*—Smooth.

*Lenticels.*—Typically with length of 2.0 mm and 9/cm2.

*Lenticel Color.*—Greyed-white 156C.

Leaves:

*Size.*—Medium.

*Average width.*—35 mm.

*Average length.*—116 mm.

*Shape.*—Lanceolate.

*Shape of tip.*—Acuminate.

*Angle of tip.*—Narrow acute.

*Shape of base.*—Obtuse.

*Margin.*—Serrate.

*Leaf Color — Upper surface.*—Green 139B.

*Leaf Color — Lower surface.*—Green 138A.

*Venation.*—Pinnate.

*Vein color.*—Yellow-green 146C.

*Surface.*—Smooth.

*Petiole.*—Medium.

*Average length.*—11.5 mm.

*Average width.*—1.8 mm.

*Petiole color.*—Yellow-green 146B.

*Glands.*—Type — Reniform.

*Size.*—Medium.

*Average length.*—1.1 mm.

*Average width.*—0.8 mm.

*Gland color*—Yellow-green 147B.

*Number.*—Typically 4 opposite each other in pairs, sometimes 3.

*Location.*—Typically on base of leaf blade and the upper end of petiole.

Flower buds:

*Hardiness.*—Hardy, under the growing conditions of Hawke's Bay, New Zealand.

*Diameter.*—1.3 mm during early dormancy (mid-June).

*Length.*—2.9 mm during early dormancy (mid-June).

*Form.*—Appressed.

*Surface.*—Pubescent.

*Color.*—Greyed-green 197B.

Flowers: Perfect, complete and containing typically a single pistil with 30–40 stamens and 5 petals and 5 sepals alternately placed. Flowers sparse.

*Type.*—Showy, large.

*Flower diameter.*—35 mm.

*Number of petals.*—Typically 5, No double blossoms observed.

*Petal shape.*—Circular.

*Petal margin.*—Slightly wavy and slightly turning inwards towards pistil.

*Petal apex.*—Rounded.

*Petal color.*—Upper surface — Red-purple 69D.

*Petal color.*—Lower surface — Red-purple 70D.

*Position of stamens compared to petals.*—below.

*Anther color.*—Red 53A.

*Position of stigma compared to anthers.*—Below.

*Fragrance.*—Slight.

*Pollen.*—Present.

*Pubescence of ovary.*—Absent.

*Bloom period.*—Mid season.

*Date of 5% flower bloom.*—Aug. 21, 2008.

*Date of full bloom* (95%).—Sep. 5, 2008.

*Length of bloom period.*—Typically 2–3 weeks under Hawke's Bay conditions.

*Flower number per node.*—Typically 1.

Fruit:
*Maturity for consumption.*—Firm ripe.
*First picking.*—Late-season.
*Size.*—Small to medium.
*Average weight.*—110 g.
*Average diameter across suture line.*—58 mm.
*Average length.*—60 mm.
*Shape* (*ventral view*).—Circular, symmetrical.
*Shape of pistil end.*—strongly pointed.
*Suture.*—Medium prominence, extends from base to apex.

Flesh:
*Ripens.*—Evenly.
*Texture.*—Firm, non-melting canning clingstone.
*Fibers.*—Non-fibrous.
*Aroma.*—Strong.
*Average soluble solids.*—20 Brix.
*Juice.*—Low to Moderate.
*Color.*—Yellow 9A. Anthocyanin coloration of flesh absent.

Stem:
*Size.*—Medium.

Skin:
*Thickness.*—Medium.
*Adherence to flesh.*—Medium to strong.
*Pubescence.*—Nil.
*Tendency to crack.*—None.
*Overcolor.*—Orange N25A blending to red N30B, with marbled to flush pattern of overcolor.
*Ground color.*—Yellow-orange 22D ground Stone:
*Type.*—Clingstone.
*Size.*—Medium to large.
*Average stone length.*—39 mm.
*Average stone width.*—25 mm.
*Average stone thickness.*—16 mm.
*Average stone weight.*—6.9 g.
*Shape* (*lateral view*).—Elliptic.
*Surface.*—Pits and grooves.
*Tendency to split.*—Very low.
*Color.*—Yellow-brown N167B.
*Use.*—Local and export markets.
*Storage.*—Good; trials indicate 2–3 weeks storage without internal breakdown of flesh.

Kernel:
*Form.*—Oval.
*Seedcoat color.*—Greyed-orange N167A.
*Viability.*—Viable.
*Seed length.*—17.1 mm.
*Seed width.*—12.6 mm at widest point.
*Seed depth.*—4.7 mm at deepest point.

Use: Dessert.

Market: Local and long distance.

Keeping quality: Excellent when held in cold storage at 0–2° C. keeping for 3 weeks without internal breakdown or significant loss of flavor.

Shipping quality: Very firm fruit which is readily handled without discernible fruit damage during picking, packing and transportation.

Plant/fruit disease resistance/susceptibility: The variety has not been tested for specific resistance or susceptibility.

Observations during planting, growing, and harvesting of fruit, under normal cultural and growing conditions of Hawke's Bay New Zealand, have not revealed any particular plant/fruit disease resistance or susceptibility. Seedlings that may be particularly susceptible to the brown rot fungus (*Monilinia fructicola*) (a common problem in stonefruit plantings in Hawke's Bay) are eliminated during the seedling stage of the breeding program.

The present new variety of nectarine tree, its flowers, foliage and fruit herein described may vary slightly in detail due to climate, soil conditions and cultural practices under which the variety may be grown. The present description is that of the variety grown under the environmental conditions prevailing near Clive, Hawke's Bay, New Zealand.

I claim:

1. A new and distinct variety of nectarine tree named 'Hortarine1', as herein illustrated and described.

* * * * *